United States Patent
Hirvonen et al.

(10) Patent No.: US 11,957,934 B2
(45) Date of Patent: Apr. 16, 2024

(54) METHODS AND SYSTEMS USING MODELING OF CRYSTALLINE MATERIALS FOR SPOT PLACEMENT FOR RADIATION THERAPY

(71) Applicant: Varian Medical Systems International AG., Cham (CH)

(72) Inventors: Petri Hirvonen, Espoo (FI); Michiko Rossi, Espoo (FI); Pierre Lansonneur, Helsinki (FI); Matti Ropo, Helsinki (FI); Viljo Petaja, Espoo (FI); Perttu Niemela, Espoo (FI); Timo Koponen, Helsinki (FI)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 410 days.

(21) Appl. No.: 16/918,949

(22) Filed: Jul. 1, 2020

(65) Prior Publication Data
US 2022/0001203 A1 Jan. 6, 2022

(51) Int. Cl.
*A61N 5/10* (2006.01)
*G16C 20/20* (2019.01)
(Continued)

(52) U.S. Cl.
CPC ........... *A61N 5/1031* (2013.01); *G16C 20/20* (2019.02); *G16H 20/40* (2018.01); *G16H 50/50* (2018.01)

(58) Field of Classification Search
CPC ...... A61N 5/103; A61N 5/1031; G16C 20/20; G16H 20/40; G16H 50/50
See application file for complete search history.

(56) References Cited

U.S. PATENT DOCUMENTS

| 4,163,901 A | 8/1979 | Azam |
| 4,914,681 A | 4/1990 | Klingenbeck et al. |

(Continued)

FOREIGN PATENT DOCUMENTS

| CN | 104001270 | 8/2014 |
| CN | 106730407 | 5/2017 |

(Continued)

OTHER PUBLICATIONS

Liao, Li, et al. "A Molecular Dynamics Approach for Optimizing Beam Intensities in IMPT Treatment Planning", Journal of Applied Mathematics and Physics. 7.9: 2130-2147. (Sep. 29, 2019) (Year: 2019).*

(Continued)

Primary Examiner — Daniel L Cerioni
(74) Attorney, Agent, or Firm — Harness, Dickey & Pierce, P.L.C.

(57) ABSTRACT

A crystalline structure modeling methodology that is conventionally used to model crystalline matter down to the atomic level is instead used to determine spot placement for radiation treatment. The cross-sectional shape of a treatment target is specified; locations (peaks) in a density field inside the shape are determined using the crystalline structure model; locations of spots in the treatment target for spot scanning are determined, where the locations correspond to the locations (peaks) inside the shape determined using the crystalline structure model; and the locations of the spots are stored as candidates for potential inclusion in a radiation treatment plan.

27 Claims, 8 Drawing Sheets

(51) Int. Cl.
*G16H 20/40* (2018.01)
*G16H 50/50* (2018.01)

(56) References Cited

U.S. PATENT DOCUMENTS

| | | |
|---|---|---|
| 5,153,900 A | 10/1992 | Nomikos et al. |
| 5,267,294 A | 11/1993 | Kuroda |
| 5,550,378 A | 8/1996 | Skillicorn et al. |
| 5,610,967 A | 3/1997 | Moorman et al. |
| 5,625,663 A | 4/1997 | Swerdloff et al. |
| 5,682,412 A | 10/1997 | Skillicorn et al. |
| 5,757,885 A | 5/1998 | Yao et al. |
| 6,198,802 B1 | 3/2001 | Elliott et al. |
| 6,222,544 B1 | 4/2001 | Tarr et al. |
| 6,234,671 B1 | 5/2001 | Solomon et al. |
| 6,260,005 B1 | 7/2001 | Yang et al. |
| 6,379,380 B1 | 4/2002 | Satz |
| 6,411,675 B1 | 6/2002 | Llacer |
| 6,445,766 B1 | 9/2002 | Whitham |
| 6,504,899 B2 | 1/2003 | Pugachev et al. |
| 6,580,940 B2 | 6/2003 | Gutman |
| 6,993,112 B2 | 1/2006 | Hesse |
| 7,268,358 B2 | 9/2007 | Ma et al. |
| 7,453,983 B2 | 11/2008 | Schildkraut et al. |
| 7,515,681 B2 | 4/2009 | Ebstein |
| 7,522,706 B2 | 4/2009 | Lu et al. |
| 7,560,715 B2 | 7/2009 | Pedroni |
| 7,590,219 B2 | 9/2009 | Maurer, Jr. et al. |
| 7,616,735 B2 | 11/2009 | Maciunas et al. |
| 7,623,623 B2 | 11/2009 | Raanes et al. |
| 7,778,691 B2 | 8/2010 | Zhang et al. |
| 7,807,982 B2 | 10/2010 | Nishiuchi et al. |
| 7,831,289 B2 | 11/2010 | Riker et al. |
| 7,835,492 B1 | 11/2010 | Sahadevan |
| 7,907,699 B2 | 3/2011 | Long et al. |
| 8,284,898 B2 | 10/2012 | Ho et al. |
| 8,306,184 B2 | 11/2012 | Chang et al. |
| 8,401,148 B2 | 3/2013 | Lu et al. |
| 8,406,844 B2 | 3/2013 | Ruchala et al. |
| 8,559,596 B2 | 10/2013 | Thomson et al. |
| 8,600,003 B2 | 12/2013 | Zhou et al. |
| 8,613,694 B2 | 12/2013 | Walsh |
| 8,636,636 B2 | 1/2014 | Shukla et al. |
| 8,644,571 B1 | 2/2014 | Schulte et al. |
| 8,716,663 B2 | 5/2014 | Brusasco et al. |
| 8,836,332 B2 | 9/2014 | Shvartsman et al. |
| 8,847,179 B2 | 9/2014 | Fujitaka et al. |
| 8,903,471 B2 | 12/2014 | Heid |
| 8,917,813 B2 | 12/2014 | Maurer, Jr. |
| 8,948,341 B2 | 2/2015 | Beckman |
| 8,958,864 B2 | 2/2015 | Amies et al. |
| 8,983,573 B2 | 3/2015 | Carlone et al. |
| 8,986,186 B2 | 3/2015 | Zhang et al. |
| 8,992,404 B2 | 3/2015 | Graf et al. |
| 8,995,608 B2 | 3/2015 | Zhou et al. |
| 9,018,603 B2 | 4/2015 | Loo et al. |
| 9,033,859 B2 | 5/2015 | Fieres et al. |
| 9,079,027 B2 | 7/2015 | Agano et al. |
| 9,149,656 B2 | 10/2015 | Tanabe |
| 9,155,908 B2 | 10/2015 | Meltsner et al. |
| 9,233,260 B2 | 1/2016 | Slatkin et al. |
| 9,258,876 B2 | 2/2016 | Cheung et al. |
| 9,283,406 B2 | 3/2016 | Prieels |
| 9,308,391 B2 | 4/2016 | Liu et al. |
| 9,330,879 B2 | 5/2016 | Lewellen et al. |
| 9,333,374 B2 | 5/2016 | Iwata |
| 9,468,777 B2 | 10/2016 | Fallone et al. |
| 9,517,358 B2 | 12/2016 | Velthuis et al. |
| 9,526,918 B2 | 12/2016 | Kruip |
| 9,545,444 B2 | 1/2017 | Strober et al. |
| 9,583,302 B2 | 2/2017 | Figueroa Saavedra et al. |
| 9,636,381 B2 | 5/2017 | Basile |
| 9,636,525 B1 | 5/2017 | Sahadevan |
| 9,649,298 B2 | 5/2017 | Djonov et al. |
| 9,656,098 B2 | 5/2017 | Goer |
| 9,694,204 B2 | 7/2017 | Hardemark |
| 9,776,017 B2 | 10/2017 | Flynn et al. |
| 9,786,054 B2 | 10/2017 | Taguchi et al. |
| 9,786,093 B2 | 10/2017 | Svensson |
| 9,786,465 B2 | 10/2017 | Li et al. |
| 9,795,806 B2 | 10/2017 | Matsuzaki et al. |
| 9,801,594 B2 | 10/2017 | Boyd et al. |
| 9,844,358 B2 | 12/2017 | Wiggers et al. |
| 9,854,662 B2 | 12/2017 | Mishin |
| 9,884,206 B2 | 2/2018 | Schulte et al. |
| 9,931,522 B2 | 4/2018 | Bharadwaj et al. |
| 9,962,562 B2 | 5/2018 | Fahrig et al. |
| 9,974,977 B2 | 5/2018 | Lachaine et al. |
| 9,987,502 B1 | 6/2018 | Gattiker et al. |
| 10,007,961 B2 | 6/2018 | Grudzinski et al. |
| 10,022,564 B2 | 7/2018 | Thieme et al. |
| 10,071,264 B2 | 9/2018 | Liger |
| 10,080,912 B2 | 9/2018 | Kwak et al. |
| 10,092,774 B1 | 10/2018 | Vanderstraten et al. |
| 10,183,179 B1 | 1/2019 | Smith et al. |
| 10,188,875 B2 | 1/2019 | Kwak et al. |
| 10,206,871 B2 | 2/2019 | Lin et al. |
| 10,212,800 B2 | 2/2019 | Agustsson et al. |
| 10,232,193 B2 | 3/2019 | Iseki |
| 10,258,810 B2 | 4/2019 | Zwart et al. |
| 10,272,264 B2 | 4/2019 | Ollila et al. |
| 10,279,196 B2 | 5/2019 | West et al. |
| 10,293,184 B2 | 5/2019 | Pishdad et al. |
| 10,307,614 B2 | 6/2019 | Schnarr |
| 10,307,615 B2 | 6/2019 | Ollila et al. |
| 10,315,047 B2 | 6/2019 | Glimelius et al. |
| 10,413,755 B1 | 9/2019 | Sahadevan |
| 10,449,389 B2 | 10/2019 | Ollila et al. |
| 10,485,988 B2 | 11/2019 | Kuusela et al. |
| 10,525,285 B1 | 1/2020 | Friedman |
| 10,549,117 B2 | 2/2020 | Vanderstraten et al. |
| 10,603,514 B2 | 3/2020 | Grittani et al. |
| 10,609,806 B2 | 3/2020 | Roecken et al. |
| 10,636,609 B1 | 4/2020 | Bertsche et al. |
| 10,660,588 B2 | 5/2020 | Boyd et al. |
| 10,661,100 B2 | 5/2020 | Shen |
| 10,682,528 B2 | 6/2020 | Ansorge et al. |
| 10,702,716 B2 | 7/2020 | Heese |
| 10,758,746 B2 | 9/2020 | Kwak et al. |
| 10,839,963 B2* | 11/2020 | Cole, Jr. ............... G16H 20/10 |
| 10,870,018 B2 | 12/2020 | Bartkoski et al. |
| 11,020,616 B2* | 6/2021 | Engwall ............... A61N 5/1043 |
| 2007/0287878 A1 | 12/2007 | Fantini et al. |
| 2008/0011945 A1 | 1/2008 | Maurer, Jr. et al. |
| 2008/0023644 A1 | 1/2008 | Pedroni |
| 2009/0063110 A1 | 3/2009 | Failla et al. |
| 2009/0287467 A1 | 11/2009 | Sparks et al. |
| 2010/0119032 A1 | 5/2010 | Yan et al. |
| 2010/0177870 A1 | 7/2010 | Nord et al. |
| 2010/0178245 A1 | 7/2010 | Arnsdorf et al. |
| 2010/0260317 A1 | 10/2010 | Chang et al. |
| 2011/0006224 A1 | 1/2011 | Maltz et al. |
| 2011/0091015 A1 | 4/2011 | Yu et al. |
| 2011/0135058 A1 | 6/2011 | Sgouros et al. |
| 2012/0076271 A1 | 3/2012 | Yan et al. |
| 2012/0157746 A1 | 6/2012 | Meltsner et al. |
| 2012/0171745 A1 | 7/2012 | Itoh |
| 2012/0197058 A1 | 8/2012 | Shukla et al. |
| 2013/0116929 A1 | 5/2013 | Carlton et al. |
| 2013/0150922 A1 | 6/2013 | Butson et al. |
| 2013/0177641 A1 | 7/2013 | Ghoroghchian |
| 2013/0231516 A1 | 9/2013 | Loo et al. |
| 2014/0107394 A1 | 4/2014 | Luan et al. |
| 2014/0177807 A1 | 6/2014 | Lewellen et al. |
| 2014/0185776 A1 | 7/2014 | Li et al. |
| 2014/0206926 A1 | 7/2014 | van der Laarse |
| 2014/0275706 A1 | 9/2014 | Dean et al. |
| 2014/0369476 A1 | 12/2014 | Harding |
| 2015/0011817 A1 | 1/2015 | Feng |
| 2015/0202462 A1 | 7/2015 | Iwata |
| 2015/0202464 A1 | 7/2015 | Brand et al. |
| 2015/0306423 A1 | 10/2015 | Bharat et al. |
| 2016/0199667 A1 | 7/2016 | Flynn et al. |
| 2016/0279444 A1 | 9/2016 | Schlosser |

(56) References Cited

U.S. PATENT DOCUMENTS

| | | | |
|---|---|---|---|
| 2016/0310764 A1 | 10/2016 | Bharadwaj et al. | |
| 2017/0028220 A1 | 2/2017 | Schulte et al. | |
| 2017/0189721 A1 | 7/2017 | Sumanaweera et al. | |
| 2017/0203129 A1 | 7/2017 | Dessy | |
| 2017/0281973 A1 | 10/2017 | Allen et al. | |
| 2018/0021594 A1 | 1/2018 | Papp et al. | |
| 2018/0043183 A1 | 2/2018 | Sheng et al. | |
| 2018/0056090 A1 | 3/2018 | Jordan et al. | |
| 2018/0099154 A1 | 4/2018 | Prieels | |
| 2018/0099155 A1 | 4/2018 | Prieels et al. | |
| 2018/0099159 A1 | 4/2018 | Forton et al. | |
| 2018/0154183 A1 | 6/2018 | Sahadevan | |
| 2018/0197303 A1 | 7/2018 | Jordan et al. | |
| 2018/0207425 A1 | 7/2018 | Carlton et al. | |
| 2018/0236268 A1 | 8/2018 | Zwart et al. | |
| 2019/0022407 A1 | 1/2019 | Abel et al. | |
| 2019/0022409 A1* | 1/2019 | Vanderstraten | A61N 5/1031 |
| 2019/0022422 A1 | 1/2019 | Trail et al. | |
| 2019/0054315 A1 | 2/2019 | Isola et al. | |
| 2019/0070435 A1 | 3/2019 | Joe Anto et al. | |
| 2019/0168027 A1 | 6/2019 | Smith et al. | |
| 2019/0198177 A1* | 6/2019 | Thomas, Jr. | G16H 30/20 |
| 2019/0255361 A1 | 8/2019 | Mansfield | |
| 2019/0299027 A1 | 10/2019 | Fujii et al. | |
| 2019/0299029 A1 | 10/2019 | Inoue | |
| 2019/0351259 A1 | 11/2019 | Lee et al. | |
| 2020/0001118 A1 | 1/2020 | Snider, III et al. | |
| 2020/0022248 A1 | 1/2020 | Yi et al. | |
| 2020/0030633 A1 | 1/2020 | Van Heteren et al. | |
| 2020/0035438 A1 | 1/2020 | Star-Lack et al. | |
| 2020/0069818 A1 | 3/2020 | Jaskula-Ranga et al. | |
| 2020/0164224 A1 | 5/2020 | Vanderstraten et al. | |
| 2020/0178890 A1 | 6/2020 | Otto | |
| 2020/0197730 A1 | 6/2020 | Safavi-Naeini et al. | |
| 2020/0254279 A1 | 8/2020 | Ohishi | |
| 2020/0269068 A1 | 8/2020 | Abel et al. | |
| 2020/0276456 A1 | 9/2020 | Swerdloff | |
| 2020/0282234 A1 | 9/2020 | Folkerts et al. | |
| 2022/0196716 A1* | 6/2022 | Anderson | G01R 29/10 |

FOREIGN PATENT DOCUMENTS

| | | | |
|---|---|---|---|
| CN | 107362464 | 11/2017 | |
| CN | 109966662 | 7/2019 | |
| CN | 111481840 | 8/2020 | |
| CN | 111481841 | 8/2020 | |
| EA | 010207 | 6/2008 | |
| EP | 0979656 | 2/2000 | |
| EP | 3338858 | 6/2018 | |
| EP | 3384961 | 10/2018 | |
| EP | 3421087 | 1/2019 | |
| EP | 3453427 | 3/2019 | |
| EP | 3586920 | 1/2020 | |
| JP | 2617283 | 6/1997 | |
| JP | 2019097969 | 6/2019 | |
| WO | 2007017177 | 2/2007 | |
| WO | 2010018476 | 2/2010 | |
| WO | 2013081218 | 6/2013 | |
| WO | 2013133936 | 9/2013 | |
| WO | 2014139493 | 9/2014 | |
| WO | 2015038832 | 3/2015 | |
| WO | 2015102680 | 7/2015 | |
| WO | 2016122957 | 8/2016 | |
| WO | 2017156316 | 9/2017 | |
| WO | 2017174643 | 10/2017 | |
| WO | 2018137772 | 8/2018 | |
| WO | 2018152302 | 8/2018 | |
| WO | WO-2019016301 A1 * | 1/2019 | A61N 5/103 |
| WO | 2019097250 | 5/2019 | |
| WO | 2019103983 | 5/2019 | |
| WO | 2019164835 | 8/2019 | |
| WO | 2019166702 | 9/2019 | |
| WO | 2019185378 | 10/2019 | |
| WO | 2019222436 | 11/2019 | |
| WO | 2020018904 | 1/2020 | |
| WO | 2020064832 | 4/2020 | |
| WO | 2020107121 | 6/2020 | |
| WO | 2020159360 | 8/2020 | |

OTHER PUBLICATIONS

Wang, Y., et al. "Phase field modeling of defects and deformation." Acta Materialia 58.4 (2010): 1212-1235. (Year: 2010).*

Lorenzo, G., et al. "Hierarchically refined and coarsened splines for moving interface problems, with particular application to phase-field models of prostate tumor growth." Computer Methods in Applied Mechanics and Engineering 319 (2017): 515-548. (Year: 2017).*

Lumpkin, A., et al. "Use of few-angstrom radiation imaging to characterize ultrabright, multi-GeV particle beams." Physical review letters 82.18 (1999): 3605. (Year: 1999).*

M. McManus et al., "The challenge of ionisation chamber dosimetry in ultra-short pulsed high dose-rate Very High Energy Electron beams," Sci Rep 10, 9089 (2020), published Jun. 3, 2020, https://doi.org/10.1038/s41598-020-65819-y.

Ibrahim Oraiqat et al., "An Ionizing Radiation Acoustic Imaging (iRAI) Technique for Real-Time Dosimetric Measurements for FLASH Radiotherapy," Medical Physics, vol. 47, Issue 10, Oct. 2020, pp. 5090-5101, First published: Jun. 27, 2020, https://doi.org/10.1002/mp.14358.

K. Petersson et al., "Dosimetry of ultra high dose rate irradiation for studies on the biological effect induced in normal brain and GBM," ICTR-PHE 2016, p. S84, Feb. 2016, https://publisher-connector.core.ac.uk/resourcesync/data/elsevier/pdf/14c/aHR0cDovL2FwaS5 lbHNIdmllci5jb20vY29udGVudC9hcnRpY2xlL3BpaS9zMDE2Nz gxNDAxNjMwMTcyNA==.pdf.

Susanne Auer et al., "Survival of tumor cells after proton irradiation with ultra-high dose rates," Radiation Oncology 2011, 6:139, Published Oct. 18, 2011, DOI: https://doi.org/10.1186/1748-717X-6-139.

Cynthia E. Keen, "Clinical linear accelerator delivers FLASH radiotherapy," Physics World, Apr. 23, 2019, IOP Publishing Ltd, https://physicsworld.com/a/clinical-linear-accelerator-delivers-flash-radiotherapy/.

Fan et al., "Emission guided radiation therapy for lung and prostate cancers: A feasibility study on a digital patient," Med Phys. Nov. 2012; 39(11): 7140-7152. Published online Nov. 5, 2012. https://www.ncbi.nlm.nih.gov/pmc/articles/PMC3505203/ doi: 10.1118/1.4761951.

Favaudon et al., "Ultrahigh dose-rate, "flash" irradiation minimizes the side-effects of radiotherapy," Cancer / Radiotherapy, vol. 19, Issues 6-7, Oct. 2015, pp. 526-531, Available online Aug. 12, 2015, https://doi.org/10.1016/j.canrad.2015.04.006.

O. Zlobinskaya et al., "The Effects of Ultra-High Dose Rate Proton Irradiation on Growth Delay in the Treatment of Human Tumor Xenografts in Nude Mice," Radiation Research, 181(2): 177-183. Published Feb. 13, 2014, DOI: http://dx.doi.org/10.1667/RR13464.1.

Bjorn Zackrisson, "Biological Effects of High Energy Radiation and Ultra High Dose Rates," Umea University Medical Dissertations, New series No. 315—ISSN 0346-6612, From the Department of Oncology, University of Umea, Umea, Sweden, ISBN 91-7174-614-5, Printed in Sweden by the Printing Office of Umea University, Umea, 1991.

P. Montay-Gruel et al., "Irradiation in a flash: Unique sparing of memory in mice after whole brain irradiation with dose rates above 100 Gy/s," Radiotherapy and Oncology, vol. 124, Issue 3, Sep. 2017, pp. 365-369, Available online May 22, 2017, doi: 10.1016/j.radonc.2017.05.003.

BW Loo et al., "Delivery of Ultra-Rapid Flash Radiation Therapy and Demonstration of Normal Tissue Sparing After Abdominal Irradiation of Mice," International Journal of Radiation Oncology, Biology, Physics, vol. 98, Issue 2, p. E16, Supplement: S Meeting Abstract: P003, Published: Jun. 1, 2017, DOI: https://doi.org/10.1016/j.ijrobp.2017.02.101.

Bhanu Prasad Venkatesulu et al., "Ultra high dose rate (35 Gy/sec) radiation does not spare the normal tissue in cardiac and splenic

(56) References Cited

OTHER PUBLICATIONS models of lymphopenia and gastrointestinal syndrome," Sci Rep 9, 17180 (2019), Published Nov. 20, 2019, DOI: https://doi.org/10.1038/s41598-019-53562-y.

P. Montay-Gruel et al., "Long-term neurocognitive benefits of FLASH radiotherapy driven by reduced reactive oxygen species," PNAS May 28, 2019, vol. 116, No. 22, pp. 10943-10951; first published May 16, 2019, https://doi.org/10.1073/pnas.1901777116.

Peter G. Maxim et al., "FLASH radiotherapy: Newsflash or flash in the pan?", Medical Physics, 46 (10), Oct. 2019, pp. 4287-4290, American Association of Physicists in Medicine, First published: Jun. 27, 2019, https://doi.org/10.1002/mp.13685.

Andrei Pugachev et al., "Pseudo beam's-eye-view as applied to beam orientation selection in intensity-modulated radiation therapy," Int. J. Radiation Oncology Biol. Phys., vol. 51, Issue 5, p. 1361-1370, Dec. 1, 2001, DOI: https://doi.org/10.1016/S0360-3016(01)01736-9.

Xiaodong Zhang et al., "Intensity-Modulated Proton Therapy Reduces the Dose to Normal Tissue Compared With Intensity-Modulated Radiation Therapy or Passive Scattering Proton Therapy and Enables Individualized Radical Radiotherapy for Extensive Stage IIIB Non-Small-Cell Lung Cancer: A Virtual Clinical Study," Int. J. Radiation Oncology Biol. Phys., vol. 77, No. 2, pp. 357-366, 2010, Available online Aug. 5, 2009, DOI: https://doi.org/10.1016/j.ijrobp.2009.04.028.

A. J. Lomax et al, "Intensity modulated proton therapy: A clinical example," Medical Physics, vol. 28, Issue 3, Mar. 2001, pp. 317-324, First published: Mar. 9, 2001, https://doi.org/10.1118/1.1350587.

Lamberto Widesott et al., "Intensity-Modulated Proton Therapy Versus Helical Tomotherapy in Nasopharynx Cancer: Planning Comparison and NTCP Evaluation," Int. J. Radiation Oncology Biol. Phys., vol. 72, No. 2, pp. 589-596, Oct. 1, 2008, Available online Sep. 13, 2008, DOI: https://doi.org/10.1016/j.ijrobp.2008.05.065.

Andrei Pugachev et al., "Role of beam orientation optimization in intensity-modulated radiation therapy," Int. J. Radiation Oncology Biol. Phys., vol. 50, No. 2, pp. 551-560, Jun. 1, 2001, Available online May 10, 2001, DOI: https://doi.org/10.1016/S0360-3016(01)01502-4.

Damien C. Weber et al., "Radiation therapy planning with photons and protons for early and advanced breast cancer: an overview," Radiat Oncol. 2006; 1: 22. Published online Jul. 20, 2006, doi: 10.1186/1748-717X-1-22.

RaySearch Laboratories, "Leading the way in cancer treatment, Annual Report 2013," RaySearch Laboratories (publ), Stockholm, Sweden, 94 pages, Apr. 2014, https://www.raysearchlabs.com/siteassets/about-overview/media-center/wp-re-ev-n-pdfs/brochures/raysearch-ar-2013-eng.pdf.

Fredrik Carlsson, "Utilizing Problem Structure in Optimization of Radiation Therapy," KTH Engineering Sciences, Doctoral Thesis, Stockholm, Sweden, Apr. 2008, Optimization and Systems Theory, Department of Mathematics, Royal Institute of Technology, Stockholm, Sweden, ISSN 1401-2294, https://www.raysearchlabs.com/globalassets/about-overview/media-center/wp-re-ev-n-pdfs/publications/thesis-fredrik_light.pdf.

Chang-Ming Charlie MA, "Physics and Dosimetric Principles of SRS and SBRT," Mathews J Cancer Sci. 4(2): 22, 2019, published: Dec. 11, 2019, ISSN: 2474-6797, DOI: https://doi.org/10.30654/MJCS.10022.

Alterego-admin, "Conventional Radiation Therapy May Not Protect Healthy Brain Cells," International Neuropsychiatric Association—INA, Oct. 10, 2019, https://inawebsite.org/conventional-radiation-therapy-may-not-protect-healthy-brain-cells/.

Aafke Christine Kraan, "Range verification methods in particle therapy: underlying physics and Monte Carlo modeling," Frontiers in Oncology, Jul. 7, 2015, vol. 5, Article 150, 27 pages, doi: 10.3389/fonc.2015.00150.

Wayne D. Newhauser et al., "The physics of proton therapy," Physics in Medicine & Biology, Mar. 24, 2015, 60 R155-R209, Institute of Physics and Engineering in Medicine, IOP Publishing, doi: 10.1088/0031-9155/60/8/R155.

S E McGowan et al., "Treatment planning optimisation in proton therapy," Br J Radiol, 2013, 86, 20120288, The British Institute of Radiology, 12 pages, DOI: 10.1259.bjr.20120288.

Steven Van De Water et al., "Towards FLASH proton therapy: the impact of treatment planning and machine characteristics on achievable dose rates," Acta Oncologica, Jun. 26, 2019, vol. 58, No. 10, p. 1462-1469, Taylor & Francis Group, DOI: 10.1080/0284186X.2019.1627416.

J. Groen, "FLASH optimisation in clinical IMPT treatment planning," MSc Thesis, Jul. 1, 2020, Erasmus University Medical Center, department of radiotherapy, Delft University of Technology, 72 pages.

Muhammad Ramish Ashraf et al., "Dosimetry for FLASH Radiotherapy: A Review of Tools and the Role of Radioluminescence and Cherenkov Emission," Frontiers in Oncology, Aug. 21, 2020, vol. 8, Article 328, 20 pages, doi: 10.3389/fphy.2020.00328.

Emil Schuler et al., "Experimental Platform for Ultra-high Dose Rate FLASH Irradiation of Small Animals Using a Clinical Linear Accelerator," International Journal of Radiation Oncology, Biology, Physics, vol. 97, No. 1, Sep. 2016, pp. 195-203.

Elette Engels et al., "Toward personalized synchrotron microbeam radiation therapy," Scientific Reports, 10:8833, Jun. 1, 2020, 13 pages, DOI: https://doi.org/10.1038/s41598-020-65729-z.

P-H Mackeprang et al., "Assessing dose rate distributions in VMAT plans" (Accepted Version), Accepted Version: https://boris.unibe.ch/92814/8/dose_rate_project_revised_submit.pdf Published Version: 2016, Physics in medicine and biology, 61(8), pp. 3208-3221. Institute of Physics Publishing IOP, published Mar. 29, 2016, https://boris.unibe.ch/92814/.

Xiaoying Liang et al., "Using Robust Optimization for Skin Flashing in Intensity Modulated Radiation Therapy for Breast Cancer Treatment: A Feasibility Study," Practical Radiation Oncology, vol. 10, Issue 1, p. 59-69, Published by Elsevier Inc., Oct. 15, 2019.

Alexei Trofimov et al., "Optimization of Beam Parameters and Treatment Planning for Intensity Modulated Proton Therapy," Technology in Cancer Research & Treatment, vol. 2, No. 5, Oct. 2003, p. 437-444, Adenine Press.

Vladimir Anferov, "Scan pattern optimization for uniform proton beam scanning," Medical Physics, vol. 36, Issue 8, Aug. 2009, pp. 3560-3567, First published: Jul. 2, 2009.

Ryosuke Kohno et al., "Development of Continuous Line Scanning System Prototype for Proton Beam Therapy," International Journal of Particle Therapy, Jul. 11, 2017, vol. 3, Issue 4, p. 429-438, DOI: 10.14338/IJPT-16-00017.1.

Wenbo Gu et al., "Integrated Beam Orientation and Scanning-Spot Optimization in Intensity Modulated Proton Therapy for Brain and Unilateral Head and Neck Tumors," Med Phys. Author manuscript; available in PMC Apr. 1, 2019 https://www.ncbi.nlm.nih.gov/pmc/articles/PMC5904040/ Published in final edited form as: Med Phys. Apr. 2018; 45(4): 1338-1350. Published online Mar. 1, 2018. doi: 10.1002/mp.12788 Accepted manuscript online: Feb. 2, 2018.

Paul Morel et al., "Spot weight adaptation for moving target in spot scanning proton therapy," Frontiers in Oncology, May 28, 2015, vol. 5, Article 119, 7 pages, doi: 10.3389/fonc.2015.00119.

Simeon Nill et al., "Inverse planning of intensity modulated proton therapy," Zeitschrift fur Medizinische Physik, vol. 14, Issue 1, 2004, pp. 35-40, https://doi.org/10.1078/0939-3889-00198.

A. Lomax, "Intensity modulation methods for proton radiotherapy," Physics in Medicine & Biology, Jan. 1999, vol. 44, No. 1, pp. 185-205, doi: 10.1088/0031-9155/44/1/014.

M Kramer et al., "Treatment planning for heavy-ion radiotherapy: physical beam model and dose optimization," Physics in Medicine & Biology, 2000, vol. 45, No. 11, pp. 3299-3317, doi: 10.1088/0031-9155/45/11/313.

Harald Paganetti, "Proton Beam Therapy," Jan. 2017, Physics World Discovery, IOP Publishing Ltd, Bristol, UK, 34 pages, DOI: 10.1088/978-0-7503-1370-4.

Shinichi Shimizu et al., "A Proton Beam Therapy System Dedicated to Spot-Scanning Increases Accuracy with Moving Tumors by

(56) References Cited

OTHER PUBLICATIONS

Real-Time Imaging and Gating and Reduces Equipment Size," PLoS One, Apr. 18, 2014, vol. 9, Issue 4, e94971, https://doi.org/10.1371/journal.pone.0094971.

Heng Li et al., "Reducing Dose Uncertainty for Spot-Scanning Proton Beam Therapy of Moving Tumors by Optimizing the Spot Delivery Sequence," International Journal of Radiation Oncology, Biology, Physics, vol. 93, Issue 3, Nov. 1, 2015, pp. 547-556, available online Jun. 18, 2015, https://doi.org/10.1016/j.ijrobp.2015.06.019.

Ion Beam Applications SA, "Netherlands Proton Therapy Center Delivers First Clinical Flash Irradiation," Imaging Technology News, May 2, 2019, Wainscot Media, https://www.itnonline.com/content/netherlands-proton-therapy-center-delivers-first-clinical-flash-irradiation.

R. M. De Kruijff, "FLASH radiotherapy: ultra-high dose rates to spare healthy tissue," International Journal of Radiation Biology, 2020, vol. 96, No. 4, pp. 419-423, published online: Dec. 19, 2019, https://doi.org/10.1080/09553002.2020.1704912.

Mevion Medical Systems, "Focus on the Future: Flash Therapy," Press Releases, Sep. 16, 2019, https://www.mevion.com/newsroom/press-releases/focus-future-flash-therapy.

Joseph D. Wilson et al., "Ultra-High Dose Rate (FLASH) Radiotherapy: Silver Bullet or Fool's Gold?", Frontiers in Oncology, Jan. 17, 2020, vol. 9, Article 1563, 12 pages, doi: 10.3389/fonc.2019.01563.

David P. Gierga, "Is Flash Radiotherapy coming?", International Organization for Medical Physics, 2020, https://www.iomp.org/iomp-news2-flash-radiotherapy/.

Abdullah Muhammad Zakaria et al., "Ultra-High Dose-Rate, Pulsed (FLASH) Radiotherapy with Carbon Ions: Generation of Early, Transient, Highly Oxygenated Conditions in the Tumor Environment," Radiation Research, Dec. 1, 2020, vol. 194, Issue 6, pp. 587-593, Radiation Research Society, Published: Aug. 27, 2020, doi: https://doi.org/10.1667/RADE-19-00015.1.

Yusuke Demizu et al., "Carbon Ion Therapy for Early-Stage Non-Small-Cell Lung Cancer," BioMed Research International, vol. 2014, Article ID 727962, 9 pages, Hindawi Publishing Corporation, published: Sep. 11, 2014, https://doi.org/10.1155/2014/727962.

Ivana Dokic et al., "Next generation multi-scale biophysical characterization of high precision cancer particle radiotherapy using clinical proton, helium-, carbon- and oxygen ion beams," Oncotarget, Aug. 30, 2016, vol. 7, No. 35, pp. 56676-56689, published online: Aug. 1, 2016, doi: 10.18632/oncotarget.10996.

Aetna Inc., "Proton Beam, Neutron Beam, and Carbon Ion Radiotherapy," 2020, No. 0270, http://www.aetna.com/cpb/medical/data/200_299/0270.html.

Nicholas W. Colangelo et al., "The Importance and Clinical Implications of FLASH Ultra-High Dose-Rate Studies for Proton and Heavy Ion Radiotherapy," Radiat Res. Author manuscript; available in PMC Jan. 1, 2021. https://www.ncbi.nlm.nih.gov/pmc/articles/PMC6949397/ Published in final edited form as: Radiat Res. Jan. 2020; 193(1): 1-4. Published online Oct. 28, 2019. doi: 10.1667/RR15537.1.

Mncent Favaudon et al., "Ultrahigh dose-rate FLASH irradiation increases the differential response between normal and tumor tissue in mice," Science Translational Medicine, Jul. 16, 2014, vol. 6, Issue 245, 245ra93, American Association for the Advancement of Science, DOI: 10.1126/scitranslmed.3008973.

"FlashRad: Ultra-high dose-rate FLASH radiotherapy to minimize the complications of radiotherapy," 2014, https://siric.curie.fr/sites/default/files/atoms/files/flashrad.pdf.

Tami Freeman, "FLASH radiotherapy: from preclinical promise to the first human treatment," Physics World, Aug. 6, 2019, IOP Publishing Ltd, https://physicsworld.com/a/flash-radiotherapy-from-preclinical-promise-to-the-first-human-treatment/.

IntraOp Medical, Inc., "IntraOp and Lausanne University Hospital Announce Collaboration in FLASH radiotherapy," Jun. 18, 2020, https://intraop.com/news-events/lausanne-university-flash-radiotherapy-collaboration/.

M.-C. Vozenin et al., "Biological Benefits of Ultra-high Dose Rate FLASH Radiotherapy: Sleeping Beauty Awoken," Clin Oncol (R Coll Radiol). Author manuscript; available in PMC Nov. 12, 2019. https://www.ncbi.nlm.nih.gov/pmc/articles/PMC6850216/ Published in final edited form as: Clin Oncol (R Coll Radiol). Jul. 2019; 31(7): 407-415. Published online Apr. 19, 2019. doi: 10.1016/j.clon.2019.04.001.

Efstathios Kamperis et al., "A FLASH back to radiotherapy's past and then fast forward to the future," J Cancer Prev Curr Res. 2019; 10(6):142-144. published Nov. 13, 2019, DOI: 10.15406/jcpcr.2019.10.00407.

P. Symonds et al., "FLASH Radiotherapy: The Next Technological Advance in Radiation Therapy?", Clinical Oncology, vol. 31, Issue 7, p. 405-406, Jul. 1, 2019, The Royal College of Radiologists, Published by Elsevier Ltd., DOI: https://doi.org/10.1016/j.clon.2019.05.011.

Swati Girdhani et al., "Abstract LB-280: FLASH: A novel paradigm changing tumor irradiation platform that enhances therapeutic ratio by reducing normal tissue toxicity and activating immune pathways," Proceedings: AACR Annual Meeting 2019; Mar. 29-Apr. 3, 2019; Atlanta, GA, published Jul. 2019, vol. 79, Issue 13 Supplement, pp. LB-280, American Association for Cancer Research, DOI: https://doi.org/10.1158/1538-7445.AM2019-LB-280.

Bazalova-Carter et al., "On the capabilities of conventional x-ray tubes to deliver ultra-high (FLASH) dose rates," Med. Phys. Dec. 2019; 46 (12):5690-5695, published Oct. 23, 2019, American Association of Physicists in Medicine, doi: 10.1002/mp. 13858. Epub Oct. 23, 2019. PMID: 31600830.

Manuela Buonanno et al., "Biological effects in normal cells exposed to FLASH dose rate protons," Radiother Oncol. Author manuscript; available in PMC Oct. 1, 2020. https://www.ncbi.nlm.nih.gov/pmc/articles/PMC6728238/ Published in final edited form as: Radiother Oncol. Oct. 2019; 139: 51-55. Published online Mar. 5, 2019. doi: 10.1016/j.radonc.2019.02.009.

N. Rama et al., "Improved Tumor Control Through T-cell Infiltration Modulated by Ultra-High Dose Rate Proton FLASH Using a Clinical Pencil Beam Scanning Proton System," International Journal of Radiation Oncology, Biology, Physics, vol. 105, Issue 1, Supplement , S164-S165, Sep. 1, 2019, Mini Oral Sessions, DOI: https://doi.org/10.1016/j.ijrobp.2019.06.187.

Inserm Press Office, "Radiotherapy 'flashes' to reduce side effects," Press Release, Jul. 16, 2014, https://presse.inserm.fr/en/radiotherapy-flashes-to-reduce-side-effects/13394/.

Eric S. Diffenderfer et al., "Design, Implementation, and in Vivo Validation of a Novel Proton FLASH Radiation Therapy System," International Journal of Radiation Oncology, Biology, Physics, vol. 106, Issue 2, Feb. 1, 2020, pp. 440-448, Available online Jan. 9, 2020, Published by Elsevier Inc., DOI: https://doi.org/10.1016/j.ijrobp.2019.10.049.

Valerie Devillaine, "Radiotherapy and Radiation Biology," Institut Curie, Apr. 21, 2017, https://institut-curie.org/page/radiotherapy-and-radiation-biology.

Imaging Technology News, "ProNova and medPhoton to Offer Next Generation Beam Delivery, Advanced Imaging for Proton Therapy," Oct. 6, 2014, Wainscot Media, Link: https://www.itnonline.com/content/pronova-and-medphoton-offer-next-generation-beam-delivery-advanced- maging-proton-therapy.

Oncolink Team, "Radiation Therapy: Which type is right for me?", OncoLink Penn Medicine, last reviewed Mar. 3, 2020, Trustees of the University of Pennsylvania, https://www.oncolink.org/cancer-treatment/radiation/introduction-to-radiation-therapy/radiation-therapy-which-type-is- right-for-me.

Marco Durante et al., "Faster and safer? FLASH ultra-high dose rate in radiotherapy," Br J Radiol 2018; 91(1082): 20170628, British Institute of Radiology, Published Online: Dec. 15, 2017, https://doi.org/10.1259/bjr.20170628.

John R. Fischer, "Pmb launches FLASH radiotherapy system for use in clinical trials," HealthCare Business News, Jun. 29, 2020, DOTmed.com, Inc., https://www.dotmed.com/news/story/51662.

Marie-Catherine Vozenin et al., "The advantage of FLASH radiotherapy confirmed in mini-pig and cat-cancer patients," Clinical Cancer Research, Author Manuscript Published OnlineFirst Jun. 6,

(56) References Cited

OTHER PUBLICATIONS 2018, https://clincancerres.aacrjournals.org/content/clincanres/early/2018/06/06/1078-0432.CCR-17-3375.full.pdf.
Meier, Gabriel, et al. "Contour scanning for penumbra improvement in pencil beam scanned proton therapy." Physics in Medicine & Biology 62.6 (2017): 2398.
Ur Rehman, Mahboob, et al. "An optimized approach for robust spot placement in proton pencil beam scanning." Physics in Medicine & Biology 64.23 (2019): 235016.

* cited by examiner

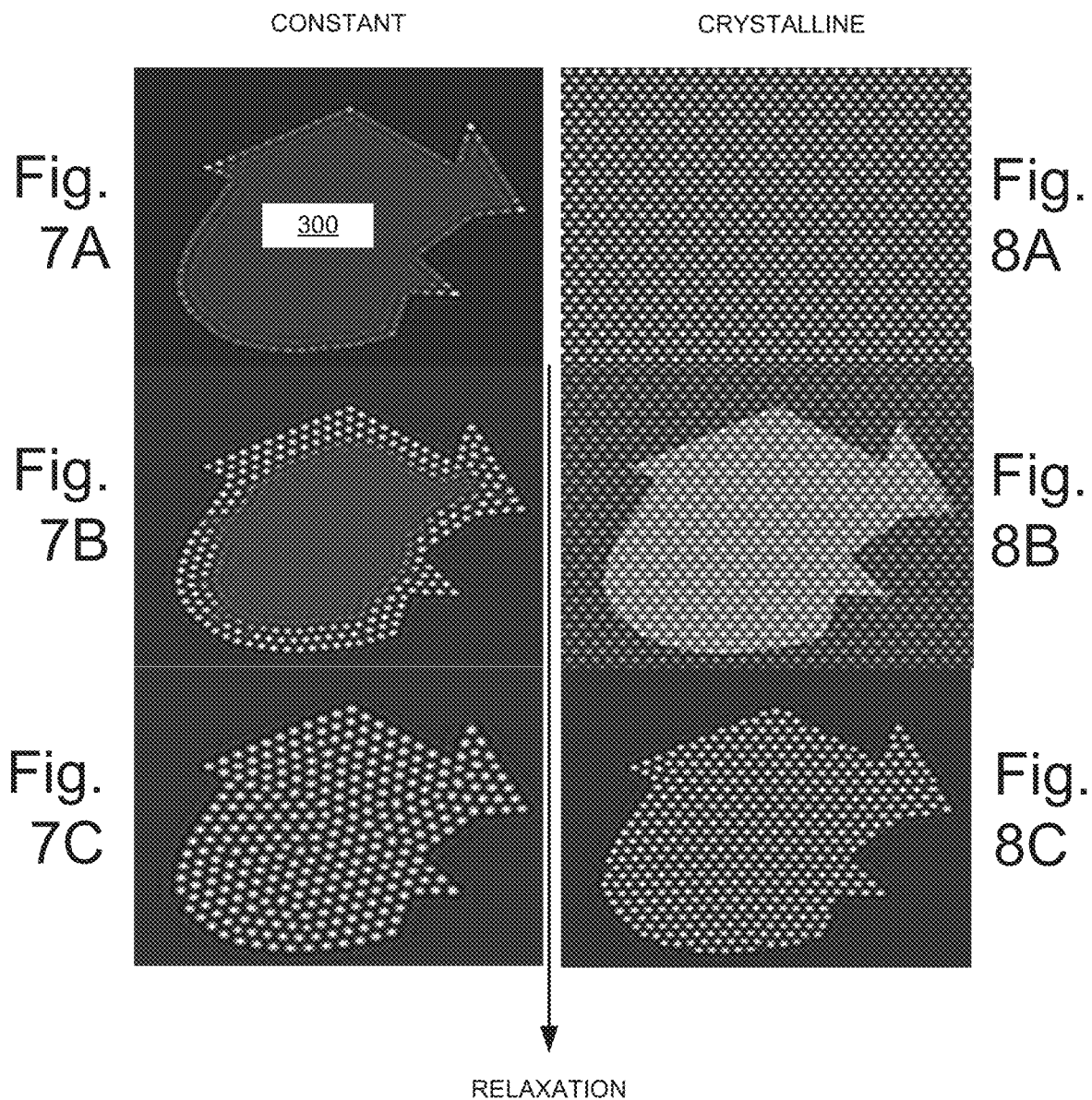

METHODS AND SYSTEMS USING MODELING OF CRYSTALLINE MATERIALS FOR SPOT PLACEMENT FOR RADIATION THERAPY

BACKGROUND

The use of radiation therapy to treat cancer is well known. Typically, radiation therapy involves directing a beam of high energy proton, photon, ion, or electron radiation into a target or volume in a treatment target of unhealthy tissue (e.g., a tumor or lesion).

Radiation therapy using proton beams has a significant advantage relative to the use of other types of beams. A proton beam reaches a depth in tissue that depends on the energy of the beam, and releases most of its energy (delivers most of its dose) at that depth. The region of a depth-dose curve where most of the energy is released is referred to as the Bragg peak of the beam.

Before a patient is treated with radiation, a treatment plan specific to that patient is developed. The plan defines various aspects of the radiation therapy using simulations and optimizations that may be based on past experiences. In general, the purpose of the treatment plan is to deliver sufficient radiation to unhealthy tissue while minimizing exposure of surrounding healthy tissue to that radiation.

One radiation therapy technique is known as spot scanning, also known as pencil beam scanning. In spot scanning, a beam is directed to spots in a treatment target prescribed by the treatment plan. The prescribed spot positions are typically arranged in a fixed (raster) pattern for each energy layer of the beam, and the beam is delivered on a fixed scanning path within an energy layer. By superposition of several beams of different energies at adjoining spots, the Bragg peaks of the beams overlap to uniformly deliver the prescribed dose across the treatment target up to the edges of the target with a sharp drop to zero dose at or just beyond the edges.

A precise calculation of the number of spots and their placement (location and distribution) is critical. The goal is to determine a spot placement that: 1) conforms to the outline of the treatment target, to improve the lateral penumbra and spare healthy tissue outside the treatment target from exposure to radiation beyond what is necessary to treat the unhealthy tissue; and 2) is uniform inside the treatment target, to avoid dose variations (dose inhomogeneity) inside the treatment target so that the prescribed dose is delivered to all parts of the target.

SUMMARY

Embodiments according to the present invention apply methodologies not conventionally used for spot placement to develop radiation treatment plans for spot scanning. In embodiments, a crystalline structure modeling methodology that is conventionally used to model crystalline matter down to the atomic level is instead used to determine spot placement for radiation treatment. Crystalline structure models include a family of models and methods that includes, but is not limited to, phase-field crystal (PFC) modeling and molecular dynamics.

A PFC model, for example, describes periodic systems such as atomic lattices using smooth classical density fields. The evolution of the model of a PFC system is governed by minimization of a free energy that is a function of a density field. The formulation and parameters of the free energy determine the lattice symmetry, elastic properties, and other features of the periodic system.

In PFC embodiments according to the invention, the solution to the problem of finding a suitable spot placement for spot scanning is cast as an iterative relaxation of the density field, which yields highly regular and edge-conformal two-dimensional (2D) lattices of density peaks, which in turn define the spot locations. More specifically, in PFC embodiments, for example, information describing a treatment target (e.g., the size and cross-sectional shape of the target) in a patient is specified; locations (peaks) in the density field inside the shape are determined using the crystalline structure model; locations of spots in the treatment target for spot scanning are determined, where the locations correspond to the locations (peaks) inside the shape determined using the crystalline structure model; and the locations of the spots are stored as candidates that can be included in a radiation treatment plan for the patient. A PFC type of model can also be solved in three dimensions to yield body-centered cubic spot patterns for even coverage within the treatment target.

Crystalline structure modeling methodology can yield spot locations and distributions that are conformal with the outlines of the treatment target and uniform inside it. Consequently, during radiation treatment, surrounding healthy tissue is spared from damaging radiation and dose variations within the target are avoided.

In general, the use of crystalline structure modeling methodologies can improve upon previous spot placement schemes. A crystalline structure model like a model based on PFC yields edge-conformal spot placements for sharper lateral penumbras and better dose distributions, allows spot placement that considers the distance from the edge of the treatment target for edge enhancement, and can yield highly regular spot placements aligned in a fast scanning direction that optimizes (reduces) the scanning time. These benefits are particularly useful for FLASH radiation therapy in which a relatively high therapeutic radiation dose is delivered to the target within a single, short period of time (e.g., dose rates of at least 40 grays in less than one second, and as much as 120 grays per second or more).

These and other objects and advantages of embodiments according to the present invention will be recognized by one skilled in the art after having read the following detailed description, which are illustrated in the various drawing figures.

This summary is provided to introduce a selection of concepts that are further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure. The drawings are not necessarily drawn to scale.

FIGS. 7A, 7B, and 7C illustrate an example of crystalline structure modeling in embodiments according to the invention.

FIGS. 8A, 8B, and 8C illustrate another example of crystalline structure modeling in embodiments according to the invention.

DETAILED DESCRIPTION

Figure 1:
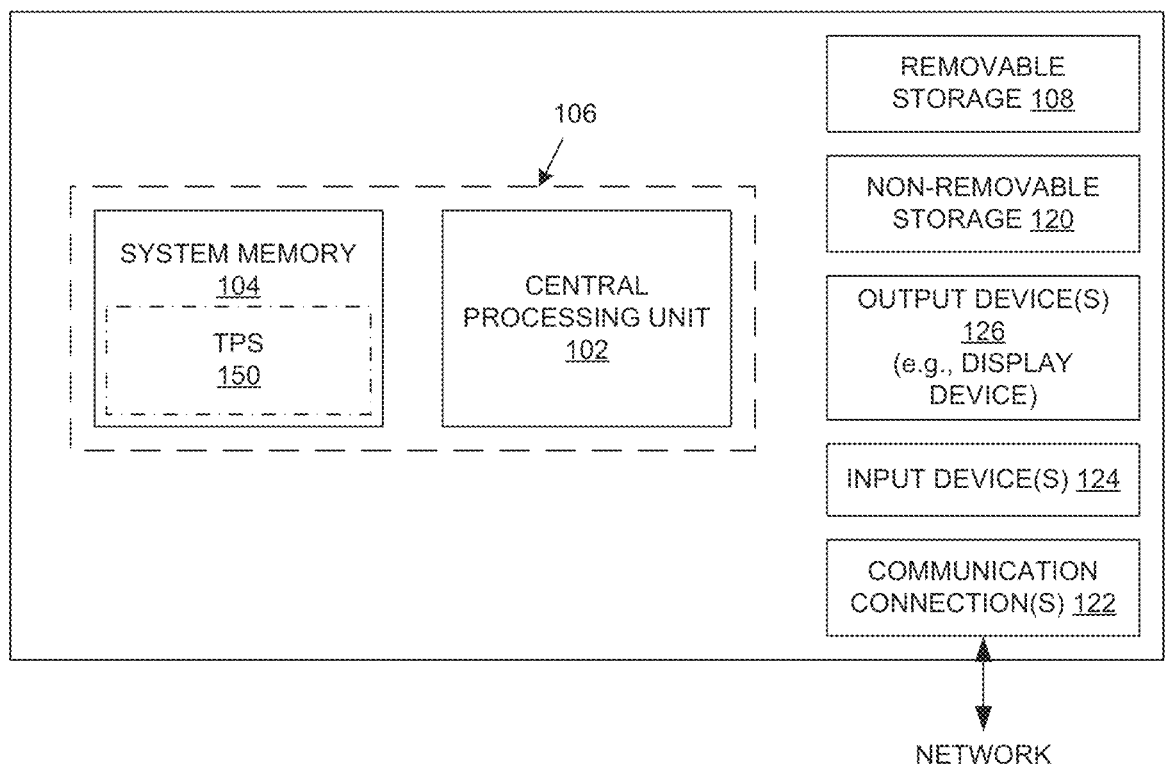
FIG. 1 is a block diagram of an example of a computer system upon which the embodiments described herein may be implemented.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "accessing," "determining," "describing," "using," "modeling," "storing," "initializing," "relaxing," "placing," "filling," "overwriting," or the like, refer to actions and processes (e.g., the flowcharts of FIGS. 2 and 5) of a computer system or similar electronic computing device or processor (e.g., the computer system 100 of FIG. 1). The computer system or similar electronic computing device manipulates and transforms data represented as physical (electronic) quantities within the computer system memories, registers or other such information storage, transmission or display devices.

The discussion to follow may include terms such as "dose," "dose rate," "energy," etc. Unless otherwise noted, a value is associated with each such term. For example, a dose has a value and can have different values. For simplicity, the term "dose" may refer to a value of a dose, for example, unless otherwise noted or apparent from the discussion.

Portions of the detailed description that follows are presented and discussed in terms of methods. Although steps and sequencing thereof are disclosed in figures herein (e.g., FIGS. 2 and 5) describing the operations of those methods, such steps and sequencing are examples only. Embodiments are well suited to performing various other steps or variations of the steps recited in the flowcharts of the figures herein, and in a sequence other than that depicted and described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory, read only memory (ROM), electrically erasable programmable ROM (EEPROM), flash memory or other memory technology, compact disk ROM (CD-ROM), digital versatile disks (DVDs) or other optical or magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

FIG. 1 shows a block diagram of an example of a computer system 100 upon which the embodiments described herein may be implemented. In its most basic configuration, the system 100 includes at least one processing unit 102 and memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 also includes input device(s) 124 such as keyboard, mouse, pen, voice input device, touch input device, etc. Output device(s) 126 such as a display device, speakers, printer, etc., are also included. A display device may be, for example, a cathode ray tube display, a light-emitting diode display, or a liquid crystal display.

In the example of FIG. 1, the memory 104 includes computer-readable instructions, data structures, program modules, and the like associated with a treatment planning system (TPS) 150. However, the treatment planning system 150 may instead reside in any one of the computer storage media used by the system 100, or may be distributed over some combination of the computer storage media, or may be distributed over some combination of networked computers. The treatment planning system 150 is used to evaluate and produce a final (prescribed) treatment plan.

In radiation therapy techniques in which the intensity of the particle beam is either constant or modulated across the field of delivery, such as in intensity modulated radiation therapy (IMRT) and intensity modulated particle therapy (IMPT), beam intensity is varied across each treatment region (volume in a treatment target) in a patient. Depending on the treatment modality, the degrees of freedom available for intensity modulation include, but are not limited to, beam shaping (collimation), beam weighting (spot scanning), number of energy layers, and angle of incidence (which may be referred to as beam geometry). These degrees of freedom lead to an effectively infinite number of potential treatment plans, and therefore consistently and efficiently generating and evaluating high-quality treatment plans is beyond the capability of a human and relies on the use of a computer system, particularly considering the time constraints associated with the use of radiation therapy to treat ailments like cancer, as well as the large number of patients that are undergoing or need to undergo radiation therapy during any given time period. For IMPT, steep dose gradients are often used at the target border and field edges to enhance dose conformity. This increases the complexity of fluence maps and decreases robustness to uncertainties.

Embodiments according to the invention improve radiation treatment planning and the treatment itself. Treatment plans generated as described herein are superior for sparing healthy tissue from radiation in comparison to conventional techniques by optimizing the balance between the dose rate delivered to unhealthy tissue (e.g., a tumor) in a volume in a treatment target and the dose rate delivered to surrounding healthy tissue. Treatment planning, while still a complex task, is improved relative to conventional treatment planning.

In summary, embodiments according to this disclosure pertain to generating and implementing a treatment plan that is the most effective (relative to other plans) and with the least (or most acceptable) side effects (e.g., a lower dose rate outside of the region being treated). Thus, embodiments according to the invention improve the field of radiation treatment planning specifically and the field of radiation therapy in general. Embodiments according to the invention allow more effective treatment plans to be generated quickly.

Embodiments according to the invention are not necessarily limited to radiation therapy techniques such as IMRT and IMPT.

A proposed radiation treatment plan is defined (e.g., using the treatment planning system 150 of FIG. 1), stored in a computer system memory, and accessed from that memory. The proposed radiation treatment plan includes values of parameters that can affect dose and dose rate, as well as other parameters. The parameters that can affect dose and dose rate include, but are not limited to, a number of irradiations of the volume in a treatment target, a duration of each of the irradiations (irradiation times), and a dose deposited in each of the irradiations. The parameters may also include angles (directions) of beams to be directed toward a treatment target, and a beam energy for each of the beams. The parameters may also include a period of time during which the irradiations are applied (e.g., a number of irradiations are applied over a period of time such as an hour, with each irradiation in the period of time separated from the next by another period of time) and an interval of time between each period of irradiations (e.g., each hour-long period is separated from the next by a day). The volume of a treatment target may be divided into sub-volumes or voxels, in which case the values of the parameters can be on a per-sub-volume or per-voxel basis (e.g., a value per sub-volume or voxel).

A control system (not shown) implemented with a computer system like the computer system of 100 can be used to implement the prescribed radiation treatment plan. The control system can control parameters of a beam-generating system, a nozzle, and a patient support device, including parameters such as the energy, intensity, direction, size, and/or shape of the beam, according to data it receives and according to the prescribed radiation treatment plan.

During treatment, in an example embodiment, a particle beam enters the nozzle, which includes one or more components that affect (e.g., decrease, modulate) the energy of the beam, to control the dose delivered by the beam and/or to control the depth versus depth curve of the beam, depending on the type of beam. For example, for a proton beam or an ion beam that has a Bragg peak, the nozzle can control the location of the Bragg peak in the treatment target. In other embodiments, energy modulation is performed outside of the nozzle (e.g., upstream of the nozzle).

In embodiments according to the invention, the nozzle emits particles in a spot scanning beam (also referred to as a pencil beam). The nozzle is mounted on a moveable gantry so that the beam can be delivered from different directions (angles) relative to a patient (treatment target) on the patient support device, and the position of the patient support device relative to the beam may also be changed. The target area is irradiated with a raster scan by the spot scanning beam. The increased flexibility made available through spot scanning greatly improves the precision of the dose delivered to a treatment, to maximize dose delivery to unhealthy tissue and minimize damage to healthy tissue.

The beam can deliver a relatively high dose rate (a relatively high dose in a relatively short period of time). For example, the beam can deliver at least 40 grays (Gy) in less than one second, and may deliver as much as 120 Gy per second or more.

Using Modeling of Crystalline Materials for Spot Placement for Radiation Therapy Embodiments according to the present invention provide improved methods that can be used for generating radiation treatment plans for radiation therapy (RT) including FLASH RT. For FLASH RT, dose rates of at least 40 Gy in less than one second, and as much as 120 Gy per second or more, may be used.

The discussion to follow is in the framework of a phase-field crystal (PFC) model. However, embodiments according to the invention are not so limited. Other types of models, such as but not limited to molecular dynamics, can be adapted for use in determining spot placements for spot scanning.

In overview, in embodiments according to the invention, the solution to the problem of finding a suitable spot placement for spot scanning is cast as an iterative relaxation of a density field, which yields highly regular and edge-conformal two-dimensional (2D) lattices of density peaks, which in turn define the spot locations for radiation therapy using spot scanning. In the discussion to follow, the term "peak" is used when discussing a location in a treatment target in the crystalline structure model, and the term "spot" is used when discussing a location in the treatment target in the resulting treatment plan. However, because the locations of the peaks define the locations of the spots, the two terms are effectively synonymous in the discussion below.

Figure 2:
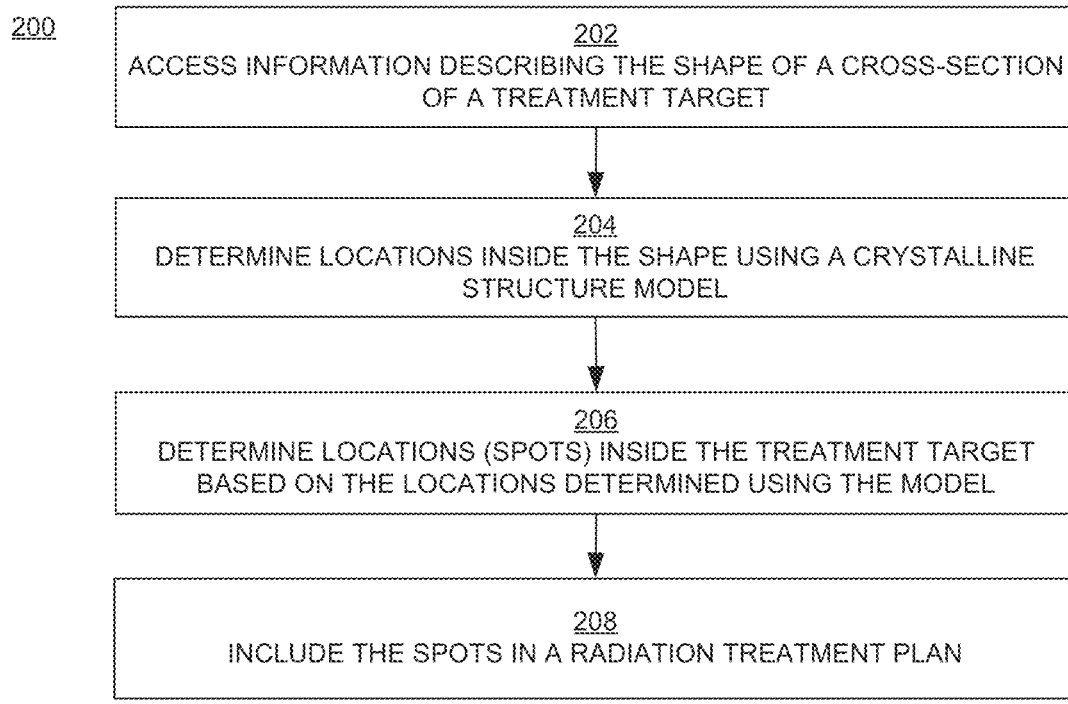
FIG. 2 is a flowchart of an example of computer-implemented operations for radiation treatment planning using a crystalline structure modeling methodology in embodiments according to the present invention.
Figure 5:
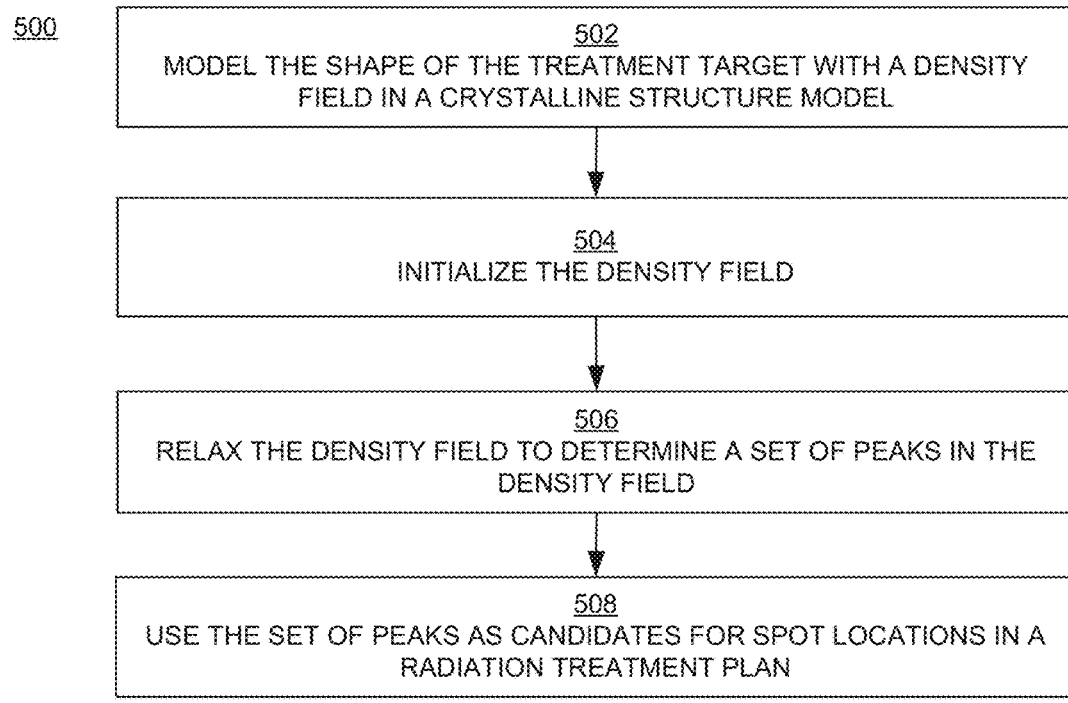
FIG. 5 is a flowchart of an example of computer-implemented operations for radiation treatment planning using a crystalline structure modeling methodology in embodiments according to the present invention.

FIGS. 2 and 5 are flowcharts 200 and 500, respectively, of examples of a computer-implemented methods that use a crystalline structure model for radiation treatment planning in embodiments according to the present invention. The flowcharts 200 and 500 can be implemented as computer-executable instructions (e.g., the treatment planning system 150 of FIG. 1) residing on some form of computer-readable storage medium (e.g., in memory of the computer system 100 of FIG. 1).

While the operations in the flowcharts of FIGS. 2 and 5 are presented as occurring in series and in a certain order, the present invention is not so limited. The operations may be performed in a different order and/or in parallel, and they may also be performed in an iterative manner. As noted above, because of the different parameters that need to be considered, the range of values for those parameters, the interrelationship of those parameters, the need for treatment plans to be effective yet minimize risk to the patient, and the need to generate high-quality treatment plans quickly, the use of the treatment planning system 150 executing consistently on the computer system 100 (FIG. 1) for radiation treatment planning as disclosed herein is important.

In block 202 of FIG. 2, information that describes the outline or shape and size of a cross-section of a treatment target is accessed from computer system memory.

Figure 3:
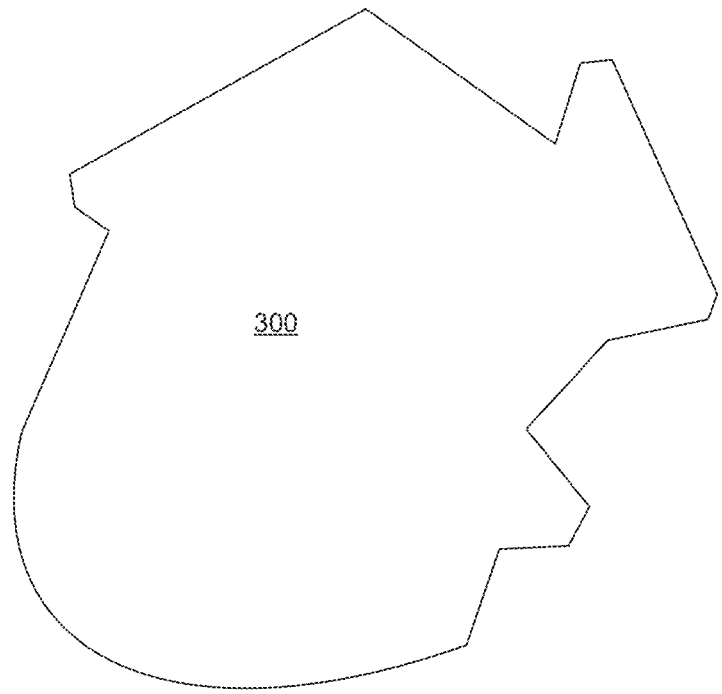
FIG. 3 illustrates an example of the shape of a cross-section of a treatment target that can be modeled using a crystalline structure modeling methodology in embodiments according to the present invention.

FIG. 3 illustrates an example of the shape 300 of a cross-section of a treatment target that can be modeled using a crystalline structure modeling methodology (e.g., a PFC model) in embodiments according to the present invention. The shape 300 can have smooth or sharp (e.g., straight) edges, boundaries, and corners that are convex or concave. In general, the shape 300 is not limited.

In block 204 of FIG. 2, locations inside the shape are determined using the crystalline structure model.

Figure 4:
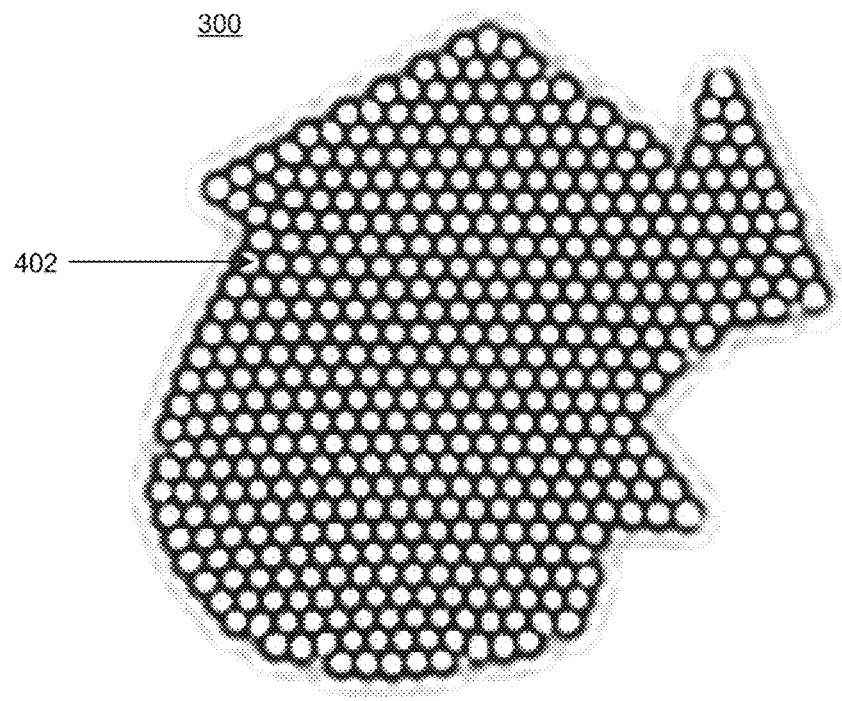
FIG. 4 is an example showing locations in a target shape determined using a crystalline structure model in embodiments according to the invention.

FIG. 4 is an example showing locations (exemplified by a location 402) in the shape 300 determined using the crystalline structure model in embodiments according to the invention. Additional information is provided in the discussion of FIG. 5.

A crystalline structure model such as a PFC model describes periodic systems such as atomic lattices using a smooth classical density field n(r). The evolution of PFC systems is governed by minimization of the free energy F(n(r)). The formulation and parameters of the free energy determine the lattice symmetry, elastic properties, and other features of the periodic system. The free energy is given by equation (1) below:

$$F = \int dr \left( \frac{R}{2} n^2 + \frac{1}{4} n^4 + \frac{1}{2} n (1 + \nabla^2)^2 n \right),$$

where the two first terms of equation (1) yield a so-called double well potential and the third term gives rise to a periodic density field n and to Hookean elasticity. Equation (1) represents one formulation of free energy; however, the invention is not so limited, and other formulations are possible and can be used instead. In 2D, this model can produce close-packed (e.g., hexagonal) structures or patterns.

Square and rectilinear structures or patterns, for example, are also possible with little increase in computational cost. Such structures can be achieved by replacing $(1+\nabla^2)^2$ with $\Pi_k(a_k(q_k^2+\nabla^2)^2+b_k)$ in equation (1), where $a_k$ and $b_k$ are weights and $q_k$ are relative length scales ($q_0$, $q_1$=1, $\sqrt{2}$ for a square lattice, for example). The computational cost is effectively the same because the above substituted term can be incorporated in a precalculated operator that may not need to be updated.

The crystalline structure model can also be extended to three dimensions (3D). The model can be solved in 3D to yield body-centered cubic spot patterns for more uniform coverage. Other structures are also possible using, for example, the substitution described above. Face-centered cubic and hexagonal close-packing also yield more uniform packing.

Calculations with the crystalline structure model begin with an initial estimate for the density field n, and then the model iteratively equilibrates the density field n and minimizes the free energy F using dissipative dynamics such as gradient descent, that given by equation (2) below:

$$\frac{\partial n}{\partial t} = -\frac{\delta F}{\delta b} = -(Rn + n^3 + (1 - \nabla^2)^2 n).$$

Equation (2) can be solved efficiently and accurately using a semi-implicit spectral method. Equation (2) is one example of dissipative dynamics; however, there are other dissipative dynamics that can be used instead, and so the invention is not so limited.

In embodiments according to the invention, the spot placement calculation is cast as a 2D calculation, where the peaks in the relaxed density field n are equated to spot positions within an energy layer of a beam for spot scanning. A chemical potential term—∫drμn, where μ=μ(r) (e.g., a spatially variable field), is added to the free energy F. A constant value μ is used inside the target, yielding a periodic density field n; that is, yielding peaks (and corresponding spots). Outside the target, µ is given a different constant value that results in a constant density field n (e.g., no peaks, and hence no spots). The region inside the target may be expanded at the expense of the region outside the target to obtain peaks (and corresponding spots) at an optimal distance from the target boundaries (edges). The dissipative dynamics are now given by equation (3) below:

$$\frac{\partial n}{\partial t} = -(Rn + n^3 + (1 + \nabla^2)^2 n - \mu).$$

Equation (3) is one example of dissipative dynamics; however, there are other dissipative dynamics that can be used instead, and so the invention is not so limited.

In block 206 of FIG. 2, the locations of spots in the treatment target for spot scanning with a radiation beam are determined based on the results of block 204. Specifically, the location of a spot for spot scanning corresponds to a location of a peak (e.g., the location 402 of FIG. 4) determined using the crystalline structure model.

In block 208, the locations of the spots for spot scanning (from block 206) can be included in a radiation treatment plan.

With reference now to FIG. 5, in block 502, the cross-section of a treatment target is modeled with the crystalline structure (e.g., PFC) model using a density field with a crystalline state inside the shape and a constant state outside the shape.

Figure 6:
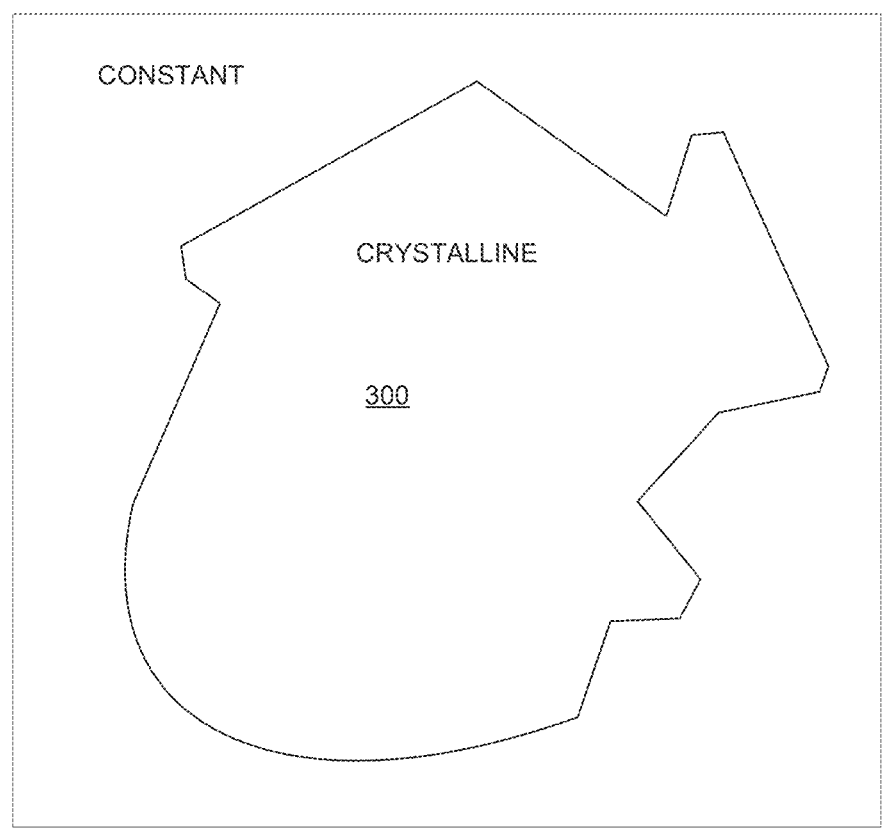
FIG. 6 is an example showing a target shape with a crystalline state inside and a constant state outside in crystalline structure modeling in embodiments according to the invention.

FIG. 6 is an example showing the shape 300 with a crystalline state inside and a constant state outside in embodiments according to the invention.

In block 504 of FIG. 5, the density field is initialized. The initial state for the density field may be, for example, a constant state, a perfect crystal state, or a hybrid of a constant state and perfect crystal state. Additional information is provided in the discussion of FIGS. 7A and 8A.

In block 506 of FIG. 5, the density field is relaxed to determine a final set of peaks in the density field. During relaxation, the free energy of the density field is minimized using dissipative dynamics such as in equation (3) above. When the density field is relaxed, the density field is allowed to evolve until it reaches equilibrium at a free energy minimum (a state where it doesn't change anymore from one iteration to the next). During relaxation, the peaks in the density field can move, grow, or wane. The final set of peaks is the set of peaks at the free energy minimum. Additional information is provided in the discussion of FIGS. 7B, 7C, 8A, and 8B.

In block 508 of FIG. 5, the final set of peaks (from block 506) can be used as candidates for spot locations in a radiation treatment plan.

FIGS. 7A, 7B, and 7C illustrate an example of crystalline structure modeling with initialization in a constant state in embodiments according to the invention. In the constant state, the density field n is initially constant, and the discontinuity in the value µ (equation (3)) at the boundaries of the target shape 300 causes nucleation of edge-conformal peaks from the initially constant density field n. FIG. 7A shows the density field after a few iterations. As the density field is relaxed, a lattice of peaks propagates inward from the boundaries of the target shape 300 by nucleation of more peaks until the shape is filled as shown in FIGS. 7B and 7C.

FIGS. 8A, 8B, and 8C illustrate an example of crystalline structure modeling with initialization in a perfect crystal state in embodiments according to the invention. In the perfect crystal initial state, the shape 300 of the treatment target is filled with a distribution of an initial set (pattern) of peaks (e.g., as a hexagonal lattice) that can extend outside the boundaries of the target shape as shown in FIG. 8A. In the example of FIG. 8A, a hexagonal lattice of peaks (from a sum of three plane waves at 120 degree angles) is used as the initial state. As the density field is relaxed, the peaks outside the target shape 300 vanish and the peaks inside the shape are rearranged to conform to the boundaries of the shape as shown in FIGS. 8B and 8C.

In the hybrid initial state, the crystalline structure model begins with a constant density field n as in the constant initial state (FIG. 7A) but, after a short relaxation (before the peaks propagate and fill the shape 300 of the treatment target), the interior of the target shape is overwritten with, for example, a hexagonal lattice as in the perfect crystal initial state (FIG. 8A). The entire interior of the shape 300 is not overwritten; for example, peaks at the edges of the target shape 300 are not overwritten. Then, the calculations with the model proceed until the interior of the target shape is filled as described above with regard to FIGS. 8B and 8C.

In other words, in the hybrid initial state, a distribution of an initial set of peaks are obtained from their nucleation and spread inward at boundaries of the shape 300 of the treatment target, the density field is relaxed to generate an additional set of peaks at locations inside target shape, at least a subset of the additional set of peaks is overwritten with a distribution of different peaks, and then the relaxing continues to determine the final set of peaks that fill the target shape.

The hybrid initial state may yield peak (and spot) placements that both are more uniform inside the treatment target and conform better to the boundaries of the target shape.

The initial state can also be selected based on or considering the scanning direction. Scanning a beam is generally significantly faster in the primary scanning direction of the beam delivery system (e.g., nozzle). That primary direction is known as the fast scanning direction. Accordingly, the orientations of the initial peaks in the perfect crystal and hybrid initial states can be chosen so that the peaks align with, for example, the rows of the fast scanning direction. To align the lattice of spots with the fast scanning direction, the density field n can be initialized based on the desired alignment. An alternative is to introduce the following term to the free energy term in equation (1). In this example, the following term favors periodicity in the x-direction:

$$\int dr \frac{1}{2} n \left(1 + \frac{\partial^2}{\partial x^2}\right)^2 n.$$

Alignment of the peaks (and hence the spots for scanning) with the fast scanning direction reduce scanning time during radiation treatments, which simplifies management of patient motion during treatment and leads to better treatment outcomes.

The resulting spot placements using the initialization from a constant state (FIGS. 7A-7C) and relaxation of the density field in a crystalline structure (FIG. 8A-8C) can be subdivided into smaller clusters to optimize the scan pattern for improved dose rates on critical regions where the field projection overlaps with projections of the organ at risk structures (see the discussion of FIG. 12 below, for example).

Figure 9:
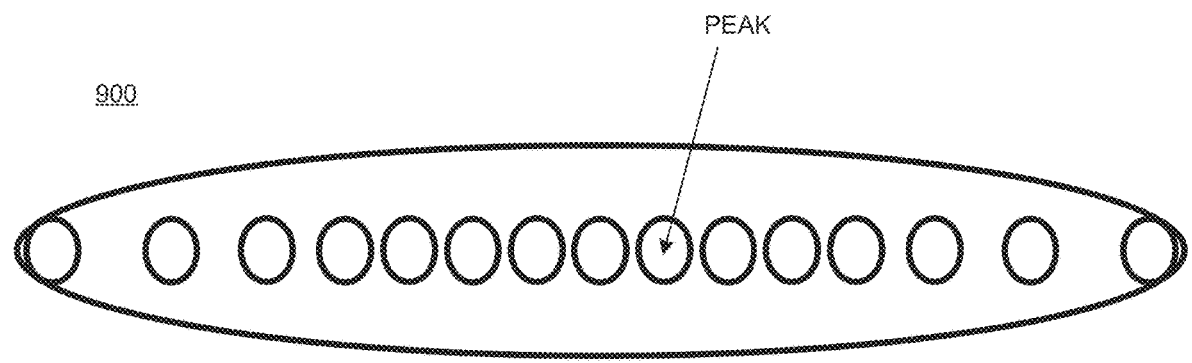
FIG. 9 illustrates an example in which the spacing of density field peaks is a function of distance from the edge of a target shape in crystalline structure modeling in embodiments according to the invention.

FIG. 9 illustrates an example in which the spacing of density field peaks (and resulting spots) is a function of distance from the edge of a target shape 900 in embodiments according to the invention. In this example, the peak (spot) spacing decreases as the distance from the boundaries of the target shape 900 increases. The spacing can be made dependent on the distance from the target boundaries by replacing the term $(1+\nabla^2)$ with the term $(q^2+\nabla^2)$, $q=q(r)$ in equation (1). Here, q is a distance map. Increased spacing at the boundaries of the target shape facilitates edge enhancement.

Figure 10:
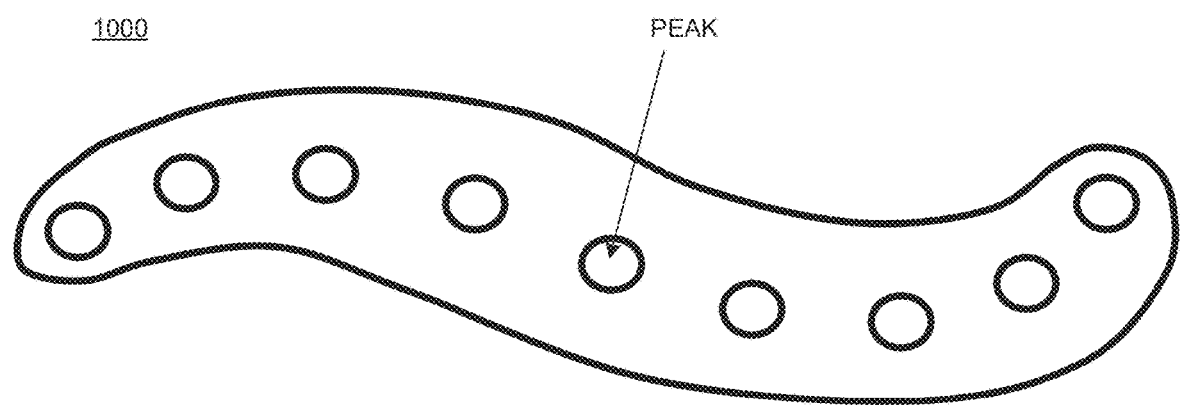
FIG. 10 illustrates an example of a non-planar energy layer in a target shape in crystalline structure modeling in embodiments according to the invention.

The example of FIG. 9 illustrates a planar energy layer in the target shape 900. However, energy layers may not be planar across the target shape. FIG. 10 illustrates an example of a non-planar energy layer in a target shape 1000 in embodiments according to the invention. In embodiments, finite-element codes may be used to determine peaks (and spots) on curved surfaces such as curved energy layers.

Figure 11A:
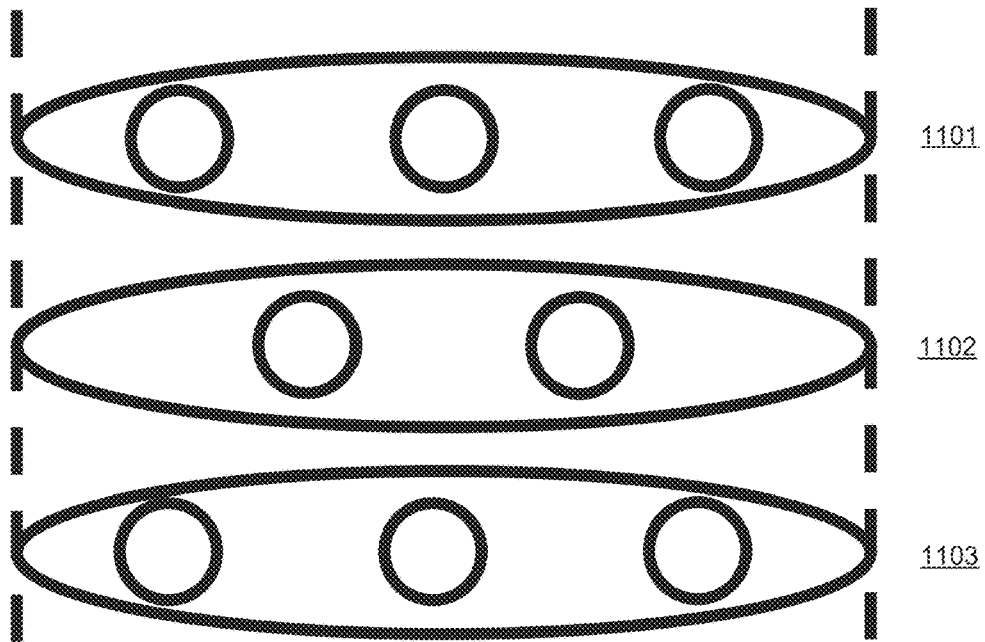
FIGS. 11A and 11B illustrate examples of multiple energy layers in a target shape in crystalline structure modeling in embodiments according to the invention.
Figure 11B:
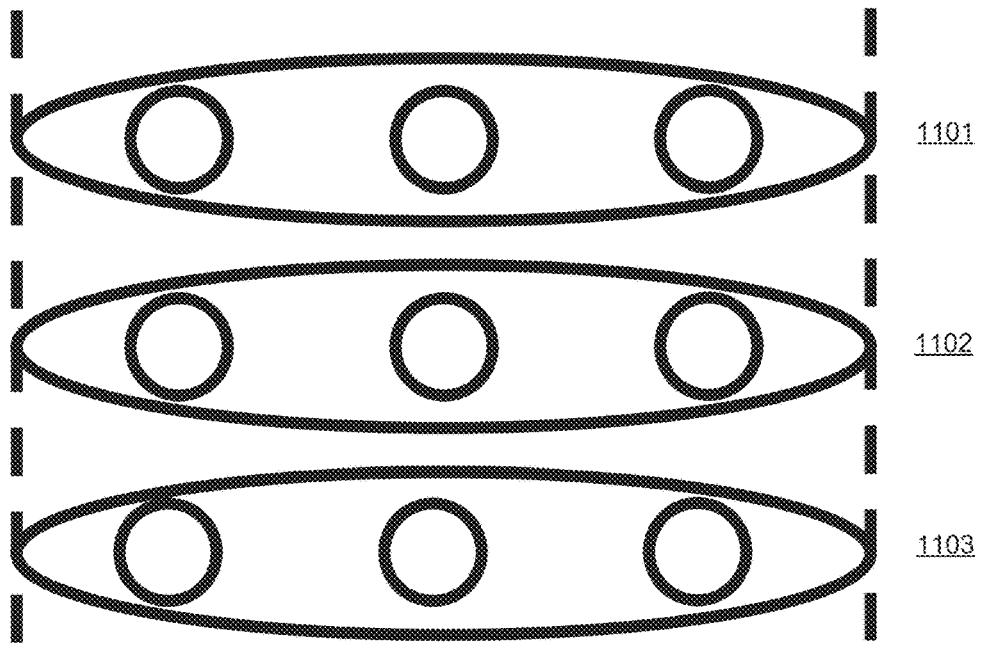

The examples of FIGS. 9 and 10 illustrate a single energy layer. FIGS. 11A and 11B illustrate examples of multiple energy layers 1101, 1102, and 1103 in the target shape 1100 in embodiments according to the invention. Three energy layers are shown, although the invention is not so limited. Note that FIGS. 11A and 11B show energy layers, not physical layers. For example, the energy layers 1101 and 1102 may be in the same physical layer, where that physical layer receives two beams of radiation during treatment, each beam having a different energy. In other examples, the energy layers 1101 and 1102 may be in different physical layers, corresponding to different Bragg peak depths.

In the example of FIG. 11A, the peaks (and resulting spots) are coupled between layers. That is, for example, the placement and location of peaks in the energy layer 1101 considers (e.g., is based on) the placement and location of peaks in the energy layer 1102. In other words, the peaks are coupled between energy layers. Coupling the peaks between energy layers allows the peaks (and corresponding spots) to be interleaved with neighboring energy layers for more uniform 3D coverage within the treatment target. In the example of FIG. 11A, the peaks in one layer are offset relative to the peaks in the adjacent layers, which also improves the uniformity of coverage and dose distribution across the treatment target during radiation treatment. The peaks in neighboring layers can be coupled by introducing the following term to the free energy term in equation (1), where n* corresponds to the density field for a neighboring energy layer:

$$\int dr\; nn^*.$$

In the example of FIG. 11B, the peaks in the layers 1101-1103 may be coupled but not necessarily so. That is, because the peaks in the energy layers 1101-1103 are aligned in this example, the distribution of peaks in any one of the energy layers can be determined independently of the distribution of peaks in the adjacent energy layers.

Figure 12:
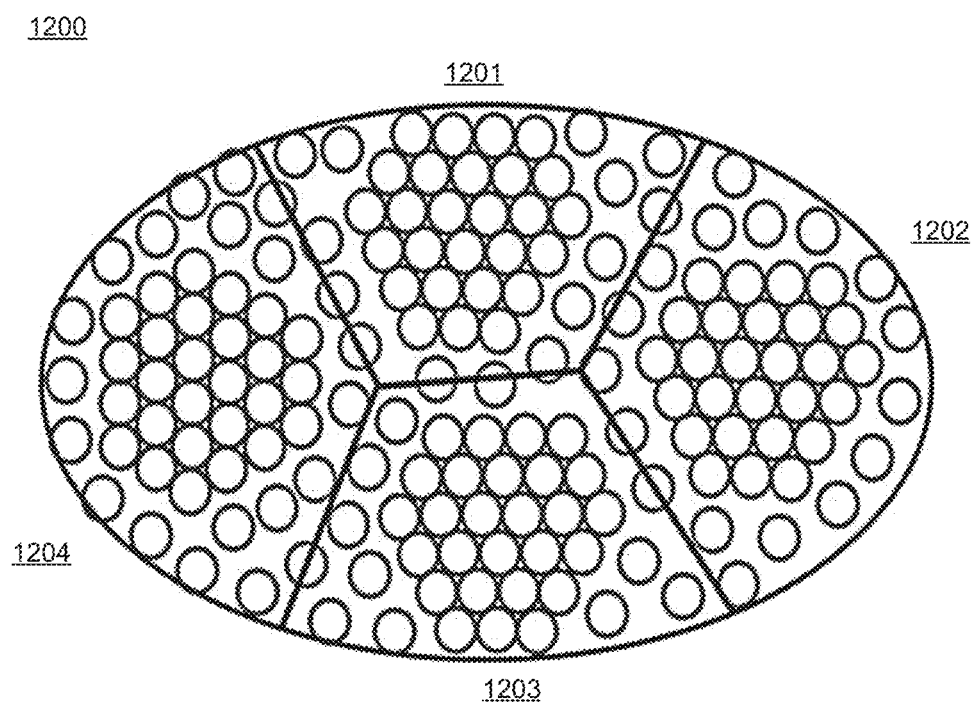
FIG. 12 illustrates an example in which a target shape is subdivided into smaller shapes for crystalline structure modeling in embodiments according to the invention.

FIG. 12 illustrates an example in embodiments according to the invention, in which a treatment target 1200 is subdivided into smaller target shapes (e.g., four smaller shapes 1201, 1202, 1203, and 1204), and the methodology described above is used to determine peak (and spot) locations with edge enhancement for each of the smaller target shapes for a given energy layer. This type of approach may reduce the overall time needed for raster scanning the treatment target 1200, by optimizing the spot distribution in each of the smaller shapes 1201-1204.

Spot clusters such as those in FIG. 12 can be achieved by replacing $(1+\nabla^2)^2$ in equation (1) with $(q^2+\nabla^2)^2$, where $q=q(r)$ is a spatially varying field indicating the distance between neighboring spots. The field q is chosen such that it is uniform inside clusters and varies at the clusters' boundaries to yield greater spot spacings there.

In summary, crystalline structure modeling methodology (e.g., PFC) can yield spot locations and distributions that are conformal with the outlines of the treatment target and uniform inside it. Consequently, during radiation treatment, surrounding healthy tissue is spared from damaging radiation and dose variations within the target are avoided.

A crystalline structure model like a model based on PFC can yield edge-conformal spot placements for sharper lateral penumbras and better dose distributions, allows spot placement that considers the distance from the edge of the treatment target for edge enhancement, and can yield highly regular spot placements aligned in the fast scanning direction and thereby optimize (reduce) the scanning time, which can be particularly useful for FLASH radiation therapy where a relatively high therapeutic radiation dose is delivered to the target within a single, short period of time. Also, a crystalline structure model like PFC does not require the outermost spots (those closest to the target boundaries) to be fixed in their location; instead, their placement can be optimized. Moreover, a crystalline structure model like PFC does not require a fixed number of peaks/spots; instead, the peaks (and corresponding spots) are free to nucleate and vanish without being constrained in any way, providing more freedom and flexibility in the optimization of the number of spots and their distribution.

In general, the use of crystalline structure modeling methodologies can improve upon previous spot placement schemes.

Embodiments according to the invention improve radiation treatment planning and the treatment itself. Treatment plans generated as described herein are superior for sparing normal tissue from radiation in comparison to conventional techniques by reducing, if not minimizing, the magnitude (and the integral in some cases) of the dose to normal tissue (outside the target) by design. When used with FLASH dose rates, management of patient motion is simplified because the doses are applied in a short period of time (e.g., less than a second). Treatment planning, while still a complex task of finding a balance between competing and related parameters, is simplified relative to conventional planning. The techniques described herein may be useful for stereotactic radiosurgery as well as stereotactic body radiotherapy with single or multiple metastases.

Embodiments according to the invention are not necessarily limited to radiation therapy techniques such as IMRT and IMPT.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:
1. A computer system, comprising:
a processor; and
a memory coupled to the processor and comprising instructions that, when executed by the processor, cause the computer system to perform a method used for planning radiation treatment, the method comprising,
acquiring information describing a shape of a treatment target;

determining locations inside the shape using a crystalline structure model;
determining locations of spots in the treatment target, the locations of the spots corresponding to the locations inside the shape determined using the crystalline structure model, and the locations of the spots being for spot scanning with a radiation beam; and
storing the locations of the spots in a radiation treatment plan.

2. The computer system of claim 1, wherein the crystalline structure model is selected from the group consisting of:
phase-field crystal modeling; and
molecular dynamics.

3. The computer system of claim 1, wherein the determining of the locations inside the shape of the treatment target and the determining of the locations of the spots in the treatment target include
modeling, with the crystalline structure model, the shape of the treatment target with a density field, the density field including a crystalline state inside the shape and a constant state outside the shape,
initializing the density field, and
relaxing the density field to determine a final set of peaks in the density field, the final set of peaks being candidates for the locations of the spots in the radiation treatment plan.

4. The computer system of claim 3, wherein the initializing of the density field includes using an initially constant density field.

5. The computer system of claim 3, wherein the initializing of the density field includes filling the shape with a distribution of an initial set of peaks at locations in the density field.

6. The computer system of claim 3, wherein the relaxing of the density field includes,
relaxing an initially constant density field to generate an additional set of peaks at locations inside the locations at boundaries of the shape,
overwriting at least a subset of the additional set of peaks with a distribution of different peaks, and
after said overwriting, continuing the relaxing of the initially constant density field to determine the final set of peaks.

7. The computer system of claim 1, wherein the determining of the locations inside the shape includes
determining the locations inside the shape considering a scanning direction of the radiation beam in the spot scanning.

8. The computer system of claim 1, wherein
the radiation beam comprises a plurality of energy layers, and
the determining of the locations inside the shape includes
determining the locations inside the shape for each of the plurality of energy layers considering the locations inside the shape that are determined for other energy layers of the plurality of energy layers.

9. The computer system of claim 1, wherein the determining of the locations inside the shape includes
determining the locations inside the shape considering a distance from boundaries of the shape.

10. A non-transitory computer-readable storage medium storing computer executable instructions that, when executed by one or more processors, cause a computer system to perform a method used for planning radiation treatment, the method comprising:
acquiring information describing a shape of a treatment target;
determining locations inside the shape using a crystalline structure model;
determining locations of spots in the treatment target, the locations of the spots corresponding to the locations inside the shape determined using the crystalline structure model, and the locations of the spots being for spot scanning with a radiation beam; and
storing, in a memory of the computer system, the locations of the spots in a radiation treatment plan.

11. The non-transitory computer-readable storage medium of claim 10, wherein the crystalline structure model is selected from the group consisting of: phase-field crystal modeling; and molecular dynamics.

12. The non-transitory computer-readable storage medium of claim 10, wherein the determining of the locations inside the shape of the treatment target and the determining of the locations of the spots in the treatment target include
modeling, with the crystalline structure model, the shape of the treatment target with a density field, the density field including a crystalline state inside the shape and a constant state outside the shape,
initializing the density field, and
relaxing the density field to determine a final set of peaks in the density field, the final set of peaks being candidates for the locations of the spots in the treatment target.

13. The non-transitory computer-readable storage medium of claim 12, wherein the initializing of the density field includes using an initially constant density field.

14. The non-transitory computer-readable storage medium of claim 12, wherein the initializing of the density field includes filling the shape with a distribution of an initial set of peaks at locations in the density field.

15. The non-transitory computer-readable storage medium of claim 12, wherein the relaxing of the density field includes
relaxing an initially constant density field to generate an additional set of peaks at locations inside the locations at boundaries of the shape,
overwriting at least a subset of the additional set of peaks with a distribution of different peaks, and
after the overwriting, continuing the relaxing of the initially constant density field to determine the final set of peaks.

16. The non-transitory computer-readable storage medium of claim 10, wherein the determining of the locations inside the shape includes
determining the locations inside the shape considering a scanning direction of the radiation beam in the spot scanning.

17. The non-transitory computer-readable storage medium of claim 10,
wherein the radiation beam comprises a plurality of energy layers, and
wherein the determining of the locations inside the shape includes
determining the locations inside the shape for each of the plurality of energy layers considering the locations inside the shape that are determined for other energy layers of the plurality of energy layers.

18. The non-transitory computer-readable storage medium of claim 10, wherein the determining of the locations inside the shape includes
determining the locations inside the shape considering a distance from boundaries of the shape.

19. A computer-implemented method used for radiation treatment planning, the computer-implemented method comprising:
- acquiring information of a treatment target, the information describing a shape of the treatment target;
- determining locations inside the shape using a crystalline structure model;
- determining locations of spots in the treatment target, the locations of the spots corresponding to the locations inside the shape determined using the crystalline structure model, and the locations of the spots being for spot scanning with a radiation beam; and
- storing the locations of the spots in a radiation treatment plan.

20. The computer-implemented method of claim 19, wherein the crystalline structure model is selected from the group consisting of: phase-field crystal modeling; and molecular dynamics.

21. The computer-implemented method of claim 19, wherein the determining of the locations inside the shape of the treatment target includes
- modeling, with the crystalline structure model, the shape of the treatment target with a density field, the density field including a crystalline state inside the shape and a constant state outside the shape,
- initializing the density field,
- relaxing the density field to determine a final set of peaks in the density field, and
- using the final set of peaks as candidates for the locations of the spots in the treatment target.

22. The computer-implemented method of claim 21, wherein the initializing of the density field includes using an initially constant density field.

23. The computer-implemented method of claim 21, wherein the initializing of the density field includes filling the shape with a distribution of an initial set of peaks at locations in the density field.

24. The computer-implemented method of claim 21, wherein the relaxing of the density field includes,
- relaxing an initially constant density field to generate an additional set of peaks at locations inside of a boundary of the shape,
- overwriting at least a subset of the additional set of peaks with a distribution of different peaks, and
- after said overwriting, continuing the relaxing of the initially constant density field to determine the final set of peaks.

25. The computer-implemented method of claim 19, wherein the determining of the locations inside the shape includes determining the locations inside the shape considering a scanning direction of the radiation beam in the spot scanning.

26. The computer-implemented method of claim 19, wherein
- the radiation beam includes a plurality of energy layers, and
- the determining of the locations inside the shape includes determining the locations inside the shape for each of the plurality of energy layers considering the locations inside the shape that are determined for other energy layers of the plurality of energy layers.

27. The computer-implemented method of claim 19, wherein the determining of the locations inside the shape includes determining the locations inside the shape considering a distance from boundaries of the shape.

* * * * *